United States Patent [19]

Schenfele

[11] Patent Number: 4,795,835

[45] Date of Patent: Jan. 3, 1989

[54] SOLVENTLESS PROCESS FOR DECONTAMINATION OF POLYACETYLENE

[75] Inventor: Robert Schenfele, Caldwell, N.J.

[73] Assignee: GAF Corporation, Wayne, N.J.

[21] Appl. No.: 163,500

[22] Filed: Mar. 3, 1988

[51] Int. Cl.$^4$ .............................................. C07C 7/00
[52] U.S. Cl. ................................... 585/809; 585/534; 585/833; 562/600
[58] Field of Search ...................... 585/534, 809, 833; 562/600

[56] References Cited

U.S. PATENT DOCUMENTS 3,493,471  2/1970  Bashaw ............................... 562/600

Primary Examiner—Curtis R. Davis
Attorney, Agent, or Firm—Marilyn J. Maue; Joshua J. Ward

[57] ABSTRACT

The process relates to the removal of copper contaminants from crude polyacetylenes containing up to 30 wt. % copper impurity by contacting a melt of the polyacetylene with aqueous hydrogen chloride to form an oil phase and an aqueous acid phase, separating said phases, treating the separated oil phase with from about 1 to about 10 volumes of water until subsequent oil and water phases are formed, agitating the separated oil phase while cooling to form a particulate product and drying said particles to recover purified polyacetylene.

11 Claims, No Drawings

SOLVENTLESS PROCESS FOR DECONTAMINATION OF POLYACETYLENE

BACKGROUND OF THE INVENTION

The synthesis of polyacetylene compounds as described in European patent 0032622 by the Glazer and Chadiot-Chadohiewicz method (Chemistry of Acetylenes by A. G. Viehe, pages 598-641) is achieved by terminal coupling of acetylenes in the presence of an alcohol diluent, i.e. methanol. Up to 600 mole % copper ion is used to effect synthesis and the crude product recovered contains from 30 to 80% polyacetylene and up to 30% copper impurity in the form of copper ion and complexed acetylides as well as unreacted amine impurities. Conventionally, for purification, the product mixture is acidified and extracted with ethyl acetate solvent, which operation requires caution due to the high flammability of the extractant. Since the liquid phases formed during the extraction with ethyl acetate solvent are not clearly defined, a significant amount of the polyacetylene is lost in the aqueous phase. Further it has been found that the copper complexed acetylene impurities, which are soluble in the methanol diluent employed in the above processes, are also extracted in the ethyl acetate phase and that removal of the ethyl acetate from product leaves behind polyacetylene product contaminated with copper impurity.

Accordingly, it is an object of this invention to overcome the above deficiencies by an economical and commercially feasible process.

Another object of this invention is to provide a polyacetylene product having greatly reduced copper acetylide contamination.

Still another object is to reduce the copper contamination of diacetylene by at least two-fold.

These and other objects of the invention will become apparent from the following description and disclosure.

THE INVENTION

In accordance with this invention there is provided a solventless process for the purification of crude, normally solid polyacetylenes containing from about 0.5 to about 30 weight % of copper impurity in the form of copper compounds and/or copper ion, which process comprises melting the polyacetylene and contacting the melt with aqueous hydrogen halide employed in an acid concentration of from about 10 weight % to 40 weight % and in a mole ratio with respect to polyacetylene of from about 1:2 and 1:10, agitating the melt-acid mixture until a two-phase liquid is formed, separating the resulting oil phase from the aqueous acid phase and agitating the separated oil phase with between about 1 and about 10 volumes of water at a pressure and temperature sufficient to maintain liquid conditions until subsequent oil and water phases are formed, separating the upper oil phase, and adding an additional volume of water, cooling the subsequent aqueous mixture with agitation to provide a suspension of polyacetylene particles, recovering and drying the resulting particles to produce a polyacetylene product wherein copper impurity is reduced at least two-fold.

In the above process, the step of contacting crude polyacetylene with aqueous hydrogen halide followed by separation of phases can be repeated one or more times with separated oil phases before contact of the final oil phase with 1-10 volumes of water. Similarly, the contact of the oil phase with water can be repeated several times before finally cooling the organic phase containing the purified polyacetylene product.

The present process efficiently removes copper contaminants which are present in the form of copper acetylides and/or copper ion as well as any other metal contaminants and also unreacted amine impurities. Reduction of polyacetylene contamination of 70-fold is commonly achieved by the present process.

The hydrogen halide employed in the above process can be a chloride, a bromide or an iodide; however hydrogen chloride is most preferred and, under optimum conditions, is employed in 15-30 wt. % concentration. The polyacetylenes subjected to puification include polyacetylenic compounds which are normally crystalline at ambient temperature and are preferably conjugated diynes, most preferably hydrocarbon or acid diynes containing from 20 to 30 carbon atoms. A general formula for these preferred acetylenic compounds is represented by the structure $A\text{-}(CH_2)_n\text{-}C{\equiv}C\text{-}C{\equiv}C\text{-}(CH_2)_m\text{-}B$ wherein m and n are both independently an integer of from 6 to 14 and A and B are independently methyl or carboxyl groups. Specific examples of such polyacetylenes include pentacosa-10,12-diynoic acid; 13,15-octacosadiyne and docosa-10,12-diyne-1, 22-dioic acid. Of these, the aged pentacosa-10,12-diynoic acid is most preferred since it provides unusually high sensitivity to electron beam exposure. It is to be understood however, that dispersions of other normally crystalline, color developing polyacetylenes having a conjugated structure can be employed alone or in admixture with the preferred diynes as the image receptive layer of the present invention. Such compounds include the diynes of the above structure wherein the A and/or B moieties, in addition to lower alkyl or carboxyl, also can be hydroxy, amido, lower alkyl substituted amido, an aliphatic or aromatic carboxylate ester group having up to 10 carbon atoms, a mono- or di- valent carboxylate metal salt group, halo, carbamyl, lower alkyl substituted carbamyl or tosyl, as well as the corresponding triyne and tetrayne products of the above polyacetylenes having from 20 to 60 carbon atoms and a conjugated structure. Examples of these compounds include 10,12-docosadiynediol, the ditoluene-p-sulfonate of 9,11-eicosadiynoic acid, the monoethyl ester of 10,12-docosadiynedioic acid, the sodium or potassium salt of 10,12-pentacosadiynoic acid, 10,12-docosadiyne chloride, 10,12-pentacosadiyne (m-tolyl- urethane), 10,12-pentacosadiyne {[(butoxycarbonyl)- methyl] urethane}, N-(dimethyl)-10,12-pentacosadiynamide, N,N'-bis(α-methylbenzyl) 10,12-pentacosadivndiamide, etc.

The purified polyacetylene compounds are suitably coated on a substrate as an image receptive layer dispersed in a binder to provide films suitable as recording media by methods generally known.

The solventless process of the present invention achieves many advantages over prior processes in addition to significant reduction of copper contamination and cost saving realized by the elimination of flammable solvent removal. More particularly, the unreacted amine is conveniently isolated in the hot hydrohalide acid solution and may then be recycled to the synthesis process feed for preparation of additional quantities of crude polyacetylene. Also, deriving from the improved contact of the hot molten crude polyacetylene with acid, greater amounts of metal can be removed with smaller volumes of liquid, thus reducing the size of equipment required for purification. Finally, product loss, associated with liquid phase decantation is virtually eliminated and the particulate product formed is of uniform spherical size easily separated from water.

A more detailed description of the process comprises melting a crude polyacetylene product containing from about 0.5 to about 10 weight % metallic impurity at a temperature between about 40° C. and about 100° C., preferably for diacetylenic compounds at a temperature between about 55° C. and about 80° C., under a pressure of from about 1 psig. to about 25 psig. and contacting the melt with aqueous hydrogen halide, preferably hydrogen chloride in aqueous solution containing from about 10 to about 40 weight % of the acid, in a mole ratio of from about 1:2 to about 1:8 hydrogen halide solution to polyacetylene. The resulting mixture is contacted under good agitation until a two phase liquid is formed, usually within a period of from about 5 to 60 minutes. The liquid is then allowed to settle into an upper oil phase containing polyacetylene and a lower aqueous acid phase containing unreacted organic material carried over from the synthesis of the crude polyacetylene. The oil phase containing product is recovered and, if desired, the above procedure involving agitation with the hydrogen halide solution and separation of the oil phase from the aqueous acid phase can be repeated. The final oil phase, separated from one or a plurality of treatments with aqueous hydrogen halide, is then agitated with between about 1 and about 10 volumes of water at a temperature sufficient to maintain the polyacetylene in a liquid state until a subsequent oil phase and water phase are formed. The oil phase containing product is then recovered from the water phase and agitation is continued while cooling to form discrete product particles of substantially uniform size and dimension. These particles are then dried to constant weight and are recovered as highly purified polyacetylene suitable for use as an imaging component on a recording media. As with the hydrogen halide treatment, the agitation with water can be repeated one or more times, with decreasing volumes if desired, when the crude polyacetylene is more highly contaminated.

Optionally, the purified polyacetylene particles of this invention can be further purified by recrystallization from an alkanol solution. In thise case, the particles are dissolved in the alkanol solvent and the resulting solution subjected to evaporation. The evaporated material can be condensed and any unreacted organic acid contained therein can be cycled to the reactor and employed for the preparation of crude polyacetylene.

Having thus described the invention, reference is now had to the accompanying examples which set forth preferred embodiments; however, these examples are not to be construed as limiting to the scope of the invention as more broadly set forth above and in the appended claims.

EXAMpLE 1

Preparation and Purifcation of Pentacosa-10,12-Diynoic Acid

A. Into a 22 liter 3-necked glass flask equipped with a reflux condenser was introduced 1,051.5 g. (7.77 moles) of 10-undecynoic acid and 323 g. (5.77 moles) of potassium hydroxide in 3790 g. (210.5 moles) of water. This mixture was stirred at a temperature of 35° C. for a period of 0.5 hour, during which 2270.0 g. (70.85 moles) of methanol diluent was added. Nitrogen was bubbled through a fritted glass tube into the stirred solution for 30 minutes, after which 939 g. (14.5 moles) of 70% aqueous ethyl amine, 100 g. (1.44 moles) of hydroxyl amine hydrochloride and 142.5 g. (1.43 moles) of cuprous chloride was added. Stirring was continued for 15 minutes and 1.850 g. (5.77 moles) of I-iodotetradecyne was added from a dropping funnel over a 30 minute period. The mixture exothermed at the following rate: $T_0$ at 48° C.; $T_{10}$ at 55° C.; $T_{15}$ at 58° C.; $T_{20}$ at 66° C. and $T_{30}$ at 68° C. Only a slight reflux of ethylamine took place during the reaction. The reaction mixture was cooled with ice water to 65° C., the pH adjusted to acidity and stirring was continued for an additional 2.5 hours. The crude pentacosa-10,12-diynoic acid was recovered in as solid beads containing about 5.4 weight % copper contamination and 20 weight % unreacted undecynoic acid and ethyl amine. B. The polyacetylene product recovered in part A is then subjected to solventless extraction by contacting 2,614 grams of polyacetylene with 11 liters of 6M hydrochloric acid at a temperature of 70° C. under good agitation in a glass separatory funnel equipped with a mechanical stirrer. After about 10 minutes, globules of oil were formed and suspended in the aqueous acid. Stirring was discontinued and an oil layer was permitted to float to the top of the funnel forming a distinct oil layer over the aqueous acid layer. The bottom aqueous acid layer was removed by suction tube and discarded. The remaining oil layer was then recontacted with 11 liters of 6M hydrochloric acid at 70° C. with agitation after which the liquid was again allowed to settle into an oil phase and an aqueous acid phase. Removal of the aqueous acid phase was repeated.

To the remaining oil phase was added 10 liters of water at 65° C. and the oil, water mixture was stirred for a period of about 0.5 hour. After oil globules became suspended in the water, stirring was discontinued, the globules were allowed to settle and the water layer was decanted and discarded. An additional 10 liters of water was then added at 65° C. with stirring and the oil globules were cooled to 30° C. and redispersed by stirring for 30 minutes after which the suspension was allowed to settle, and water removed by filtration. Easily filterable product beads were formed without the aid of solvent. The beads were recovered and dried to a white color. Analysis by atomic absorption showed tbe product contained less than 0.2 weight % copper, a reduction of greater than 250-fold from the original, 5.4 weight % copper contamination.

It will be understood from the above description and disclosure that many alterations and variations can be made in the above example. For example aqueous solutions of hydrogen bromide or hydrogen iodide could be substituted in the above example to provide beneficial results. Also, it will be recognized that other polyacetylenes containing copper contamination can be substituted for pentacosa-diynoic acid to greatly reduce metal and amine contamination.

Having thus described the invention, what is claimed is:

1. A solventless process for the purification of a crude normally solid polyacetylene containing up to 30 weight % of a copper impurity in the form of a copper compound or copper ion which comprises: melting the solid polyacetylene and contacting said melt with aqueous hydrogen halide in a concentration of from about 10 weight % to about 40 weight % acid and in a mole ratio of polyacetylene to hydrogen halide of from about 2:1 to about 10:1; agitating the resulting liquid mixture at melt temperature until an oil phase and an aqueous acid phase is formed; separating said oil phase and agitating said oil phase with between about 1 and about 10 times its volume of water at a temperature at least sufficient to maintain the polyacetylene in the liquid state; maintaining said agitation until a subsequent oil phase and a water phase is formed, separating the upper oil phase and adding an additional volume of water and cooling the subsequent mixture while agitating to form solid discrete particles of purified polyacetylene product in uniform size, isolating and drying said polyacetylene particles.

2. The process of claim 1 wherein the first formed upper oil phase separated from said lower aqueous acid phase is recontacted with aqueous hydrogen halide solution in said concentration during agitation to form a second oil phase and a second aqueous acid phase; and separating the second oil phase from said second aqueous acid phase before treatment with between about 1 and about 10 times its volume of water.

3. The process of claim 1 wherein the treatment with water is repeated on the oil phase which is separated from said water phase before cooling the resulting liquid.

4. The process of claim 1 wherein said copper impurity is essentially in the form of copper complexed acetylenes.

5. The process of claim 4 wherein the crude normally solid polyacetylene containing copper impurity also contains amine contamination and said amine is separated from said polyacetylene along with copper impurities in the treatment with aqueous hydrogen halide by the removal of the lower aqueous acid phase.

6. The process of claim 1 wherein said hydrogen halide is hydrogen chloride.

7. The process of claim 1 wherein said polyacetylene is a diacetylene.

8. The process of claim 7 wherein said diacetylene is pentacosa-diynoic acid.

9. The process of claim 1 wherein the polyacetylene is a diacetylene and said diacetylene is melted at a temperature of between about 55° C. and about 80° C.

10. The process of claim 1 wherein said dried purified polyacetylene product contains an organic acid from which the crude polyacetylene was synthesized.

11. The process of claim 10 wherein the dried purified polyacetylene product is dissolved in an aqueous alkanol solution and recrystallized by evaporation, the vapors are condensed and any of said unreacted organic acid contained therein is cycled to the process for the synthesis of crude polyacetylene.

* * * * *